United States Patent [19]

Merkle et al.

[11] Patent Number: 5,128,480
[45] Date of Patent: Jul. 7, 1992

[54] PREPARATION OF 3-METHYLPYRAZOLE

[75] Inventors: Hans R. Merkle, Ludwigshafen; Erich Fretschner, Neckarsteinach, both of Fed. Rep. of Germany

[73] Assignee: BASF Aktiengesellschaft, Ludwigshafen, Fed. Rep. of Germany

[21] Appl. No.: 745,177

[22] Filed: Aug. 15, 1991

[30] Foreign Application Priority Data

Sep. 7, 1990 [DE] Fed. Rep. of Germany ....... 4028393

[51] Int. Cl.⁵ .......................................... C07D 231/12
[52] U.S. Cl. ................................................... 548/373
[58] Field of Search ......................................... 548/373

[56] References Cited

U.S. PATENT DOCUMENTS

| | | | |
|---|---|---|---|
| 4,423,225 | 12/1983 | Lantzsch et al. | 548/373 |
| 4,424,364 | 1/1984 | Goetz et al. | 548/373 |
| 4,434,292 | 2/1984 | Heinemann et al. | 548/373 |
| 4,996,327 | 2/1991 | Merkle et al. | 548/373 |

Primary Examiner—Robert W. Ramsuer
Attorney, Agent, or Firm—Oblon, Spivak, McClelland, Maier & Neustadt

[57] ABSTRACT

3-Methylpyrazole and its derivatives are prepared by reacting butenediols or ethynylalkylcarbinols or their acylates in 30–100% by weight sulfuric acid with unsubstituted or substituted hydrazine or its salts in the presence of catalytic amounts of iodine or an iodine compound.

4 Claims, No Drawings

PREPARATION OF 3-METHYLPYRAZOLE

The process for preparing 3-methylpyrazole and its derivatives of the formula I

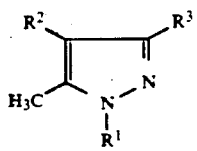

where $R^1$, $R^2$ and $R^3$ are each hydrogen or alkyl, cycloalkyl, aryl or aralkyl.

"The Chemistry of Heterocyclic Compounds" Vol. 22, chapters 3 and 5 describes many ways of synthesizing pyrazole, eg. condensation of $\alpha,\beta$-dicarbonyl compounds with hydrazines, reaction of ethynylcarbonyl compounds with hydrazines, condensation of hydrazinoacetic esters with 1,2-diketones or reaction in the presence of $ZnCl_2$.

The dehydrogenation of 2-pyrazoline to the pyrazole has also been disclosed, using chlorine or alkali metal or alkaline earth metal hypochlorites (DE-A 30 35 395), using sulfur or selenium (DE-A 30 29 160) or using aqueous hydrogen peroxide (DE-A 34 15 385). The thermal gas-phase dehydrogenation of 2-pyrazoline on palladium or platinum catalysts (DE-A 32 09 148) and the thermolysis of N-sulfonyl-2-pyrazoline to the pyrazole (DE-A 30 35 394) have also been disclosed. The older German application P 39 18 979.1 describes the dehydrogenation of 2-pyrazoline in sulfuric acid in the presence of iodine compounds.

However, the processes described above are industrially unsatisfactory, whether because the yields are only moderate, because the industrial implementation is difficult, because the starting materials are complicated and difficult to obtain, because the use of very powerful oxidizing agents or costly catalysts is necessary, because the formation of toxic by-products such as hydrogen sulfide or selenide is unavoidable, or because the preparation of N-substituted pyrazoles is impossible.

It is an object of the present invention to make 3-methylpyrazole and its derivatives available in an industrially more straightforward and economic way.

We have found that this object is achieved by a process for preparing 3-methylpyrazole and its derivatives of the formula I

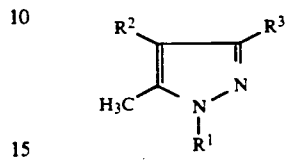

where $R^1$, $R^2$ and $R^3$ are each hydrogen or alkyl, cycloalkyl, aryl or aralkyl, which comprises reacting 2-butene-1,4-diol, 1-butene-3,4-diol or their acylates or ethynylalkylcarbinols of the formula II

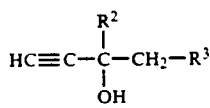

or their acylates in 30%-100% by weight sulfuric acid with unsubstituted or substituted hydrazine of the formula III

where $R^1$ has the abovementioned meaning, or its salts, in the presence of catalytic amounts of iodine or an iodine compound.

The reaction is depicted below for the case where hydrazine hydrate and 2-butene-1,4-diol are used with hydrogen iodide as catalyst,

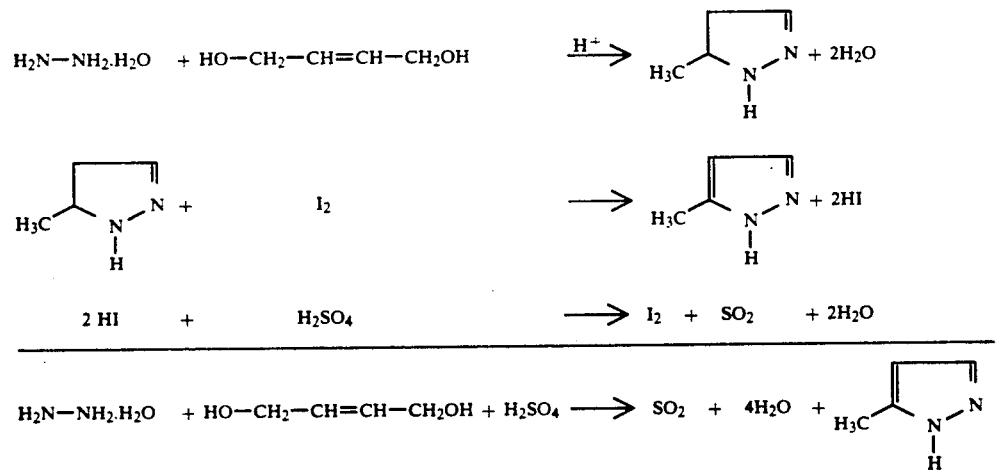

The reaction of hydrazine hydrate with 3-methyl-1-pentyn-3-ol is depicted below:

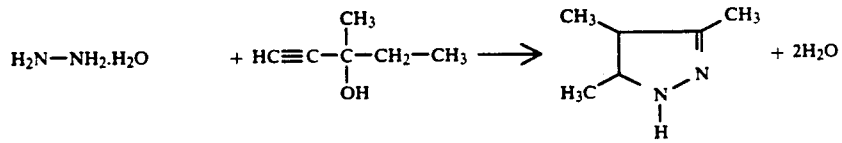

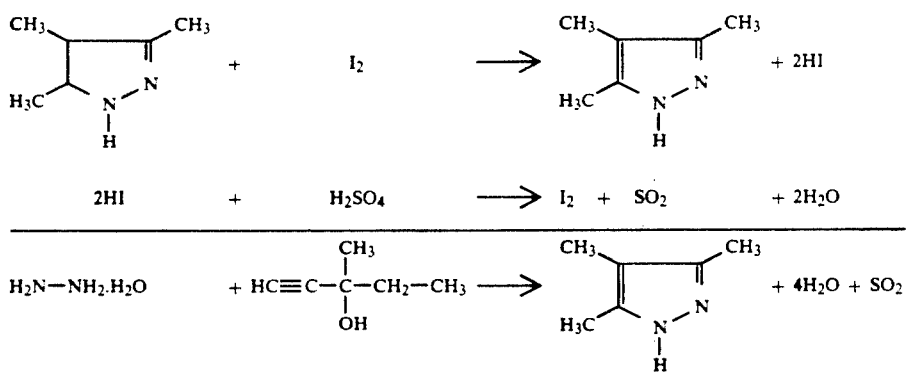

The process according to the invention can be used advantageously to prepare 3-methylpyrazoles in very good yields in a one-pot process in an industrially straightforward manner.

Examples of suitable starting materials for the synthesis are: 2-butene-1,4-diol, 1-butene-3,4-diol, 2-butene-1,4-diol diacetate, 2-butene-1,4-diol, dipropionate, 1-butene-3,4-diol diacetate, 1-butene-3,4-diol dipropionate, 1-butyn-3-ol, 1-pentyn-3-ol, 1-hexyn-3-ol, 1-heptyn-3-ol, 3-methyl-1-butyn-3-ol, 3-ethyl-1-butyn-3-ol, 3-propyl-1-butyn-3-ol, 3-methyl-1-pentyn-3-ol, 3-ethyl-1-pentyn-3-ol, 3-propyl-1-pentyn-3-ol, 3-methyl-1-hexyn-3-ol, 3-ethyl-1-hexyn-3-ol, 3-propyl-1-hexyn-3-ol, 3-methyl-1-heptyn-3-ol, 3-ethyl-1-heptyn-3-ol, 3-propyl-1-heptyn-3-ol, 4-cyclohexyl-1-butyn-3-ol, 4-cyclohexyl-3-methyl-1-butyn-3-ol, 4-cyclohexyl-1-pentyn-3-ol, and the corresponding acylates such as acetates, propionates etc. The nature of the acid component is unimportant in this connection. Besides esters of aliphatic carboxylic acids such as $C_1$-$C_8$-alkanecarboxylic acids, it is also possible to use esters of aromatic or araliphatic acids. The choice will be based primarily on availability, price and removability from the reaction mixture.

Suitable as second reaction component are, besides hydrazine, $C_1$-$C_8$-alkylhydrazines and $C_3$-$C_8$-cycloalkylhydrazines such as methyl-, ethyl-, propyl-, isopropyl-, butyl-, isobutyl-, t-butyl-, cyclopropyl-, cyclobutyl-, cyclopentyl- or cyclohexylhydrazine. It is likewise possible to use arylhydrazines or aralkylhydrazines such as phenylhydrazine and phenyl-$C_1$-$C_4$-alkylhydrazines, it also being possible for the phenyl to be substituted in each case, eg. by halogen such as fluorine, chlorine or bromine, $C_1$-$C_4$-alkyl or $C_1$-$C_4$-alkoxy, examples being phenyl- and benzylhydrazine.

In place of the free hydrazine bases it is also possible to use their hydrates or salts with mineral acids, eg. sulfuric acid, hydrochloric acid or phosphoric acid.

Suitable meanings of $R^2$ and $R^3$ are, besides hydrogen, $C_1$-$C_8$-alkyl, in particular $C_1$-$C_4$-alkyl, and the meanings given for $R^1$.

Besides elemental iodine, suitable catalysts are iodine compounds such as hydrogen iodide, alkali metal and alkaline earth metal iodides such as those of lithium, sodium, potassium, cesium, magnesium and calcium, and other metal iodides; it is also possible to use other inorganic iodine compounds such as alkali metal and alkaline earth metal hypoiodides, iodites, iodates and periodates or organic iodine compounds such as alkyl iodides, eg. methyl iodide.

Sulfuric acid is used as oxidizing agent and as condensation catalyst and can be employed in various concentrations. Suitable concentrations are from 30% to 100% by weight, preferably from 45 to 90% by weight.

The reaction is expediently carried out in such a way that 1 mole of the appropriate hydrazine is heated with from 0.5 to 2, in particular 0.8 to 1.5, moles of butenediol or alkynylalkylcarbinol at from 50° to 250° C., in particular 80° to 200° C., preferably 110° to 170° C., in sulfuric acid in the presence of catalytic amounts of an iodine compound, it being possible to remove part of the water which is present and then formed in the reaction mixture by distillation.

However, it is also possible to carry out the reaction under elevated pressure in less concentrated sulfuric acid or at correspondingly higher temperature, or under reduced pressure in more concentrated sulfuric acid or at correspondingly lower temperature.

Iodine or the iodine compound is generally employed in this reaction in amounts of from 0.01 to 10 mol %, in particular 0.05 to 5 mol %, based on hydrazine.

The reaction can be carried out in such a way that all the reactants are stirred in a vessel and heated to the reaction temperature, or by feeding the reactants as mixture or separately into a preheated vessel, or by initially introducing part of the reactants at the reaction temperature and adding the remainder dropwise.

It is also possible for sulfuric acid itself or hydrazine/sulfuric acid to be initially introduced into the vessel, which is then heated to the reaction temperature, water distilling out. The start of pyrazole formation is evident from the evolution of sulfur dioxide. Absorption of the sulfur dioxide in sodium hydroxide solution results in equimolar amounts of sodium bisulfite solution of high purity.

Cooling the reaction mixture results in the pyrazole crystallizing as the salt with sulfuric acid.

Most of the iodide which is employed is present in the form of hydrogen iodide, which can be reused, in the water which is distilled out. Working up is by neutralization of the dark-brown reaction mixture, e.g. with sodium hydroxide solution, ammonia or other inorganic bases, and extraction several times with a solvent. The extracts are dried and evaporated to dryness to yield the pyrazoles in 85%-98% purity, it being possible to increase the purity by distillation or recrystallization.

The neutralized reaction mixture can also be worked up by distillation, the distillate being composed of water and pure pyrazole and the residue of sodium sulfate (or ammonium sulfate) contaminated by organic by-products. The impure ammonium sulfate obtained as residue from the distillation on neutralization with ammonia can be oxidized to nitrogen and sulfur dioxide.

The latter can be converted via $SO_3$ back into sulfuric acid.

The process can be carried out continuously or batchwise, under atmospheric, superatmospheric or slightly subatmospheric pressure.

The pyrazoles I which can be prepared by the process according to the invention are starting materials for organic syntheses, e.g. of pharmaceutical products and crop protection agents.

EXAMPLE 1

A mixture of 100 g (2 mol) of hydrazine hydrate, 193.6 g (2.2 mol) of 2-butene-1,4-diol and 1.5 g of sodium iodide was added over the course of 90 minutes to a solution of 0.5 g of sodium iodide in 539.0 g of 80% strength sulfuric acid (4.4 mol) at 120° C. After about 70 minutes, removal of water by distillation was started and the mixture was gradually heated to 155° C.

240 g of water were distilled out. After the addition was complete, the mixture was stirred at 155° C. for 30 minutes, then cooled to 70° C., neutralized with 775 g of 25% strength sodium hydroxide solution and extracted with 1,2-dichloroethane.

The combined extracts were dried over sodium sulfate, filtered and evaporated. 155.1 g of brown oil were obtained and distilled under reduced pressure to yield 124.3 g of colorless liquid of boiling point 109° C. (35 torr) which was identified, by comparing the physicochemical data with those of a comparison sample, as 3(5)-methylpyrazole.

EXAMPLE 2

A mixture of 2 g of sodium iodide and 100 g (2.0 mol) of hydrazine hydrate was added to 718.7 g of 60% strength sulfuric acid (4.4 mol). 378.4 g (2.2 mol) of 1-butene-3,4-diol diacetate were then added dropwise at 90° C. over the course of 30 minutes. The mixture was heated, removing water by distillation, to 140° C. over the course of 3 hours. It was then stirred at 140° C. for a further half hour. A total of 680 g of water/acetic acid was distilled out. The mixture was cooled to 70° C., neutralized with 1240 g of 15% strength sodium hydroxide solution and extracted 4 times with 1,2-dichloroethane. The combined organic extracts were dried over sodium sulfate, filtered and evaporated. 178.3 g of a brown oil were obtained and distilled under reduced pressure to yield 118 g of 3-methylpyrazole.

EXAMPLE 3

A solution of 1 g of sodium iodide in 50 g (1 mol) of hydrazine hydrate was added dropwise to 431.2 g of 50% strength sulfuric acid (2.2 mol). The resulting suspension was heated to 90° C. and 107.8 g (1.1 mol) of 3-methyl-1-pentyn-3-ol were added dropwise over the course of 30 minutes. The mixture was heated to 140° C., removing a total of 210 g of water by distillation, over the course of 100 minutes. Another gram of sodium iodide was added and the mixture was heated to 150° C. and stirred at this for 15 minutes. A total of 240 g of water was distilled out. The mixture was then cooled to 70° C. and neutralized with 575 g of 15% strength sodium hydroxide solution. The neutralized reaction mixture was extracted 4 times with 1,2-dichloroethane.

The combined extracts were dried over sodium sulfate, filtered and evaporated. 114.8 g of a brown oil were obtained and dissolved in 210 g of 15% strength sulfuric acid and, after addition of active carbon, stirred.

The active carbon was filtered off and the filtrate was made alkaline with 15% strength sodium hydroxide solution, which precipitated a solid which melted at 152° C. and was identified by elemental analysis, IR, NMR and mass spectra as 3,4,5-trimethylpyrazole.

EXAMPLE 4

40 g (1 mol) of methylhydrazine and 1 g of sodium iodide were added to 308.0 g of 70% strength sulfuric acid (2.2 mol). 96.8 g (1.1 mol) of 2-butene-1,4-diol were added dropwise to this at 120° C. over the course of 90 minutes. The mixture was heated to 130° C., removing water by distillation, over the course of half an hour and was stirred at this temperature for a further half hour. A total of 155 g of water was distilled out. The reaction mixture was then neutralized at 70° C. with 655 g of 15% strength sodium hydroxide solution and extracted with 1,2-dichloroethane. The combined organic extracts were dried, filtered and evaporated. 58.5 g of a brownish red oil were obtained.

Distillation under reduced pressure resulted in a 51% yield of a liquid of boiling point 81° C. (90 torr), which was identified by IR and NMR spectra as a 1:1 mixture of 1,3- and 1,5-dimethylpyrazole.

EXAMPLE 5

46 g (1 mol) of methylhydrazine and 1 g of sodium iodide were added to 431.2 g of 50% strength sulfuric acid (2.2 mol). 107.8 g (1.1 mol) of 3-methyl-1-pentyn-3-ol were added dropwise at 90° C. over the course of 30 minutes, and the mixture was heated to 155° C. over the course of 105 minutes. During this and the subsequent 30 minutes of stirring a total of 280 g of water were distilled out. The reaction solution was then diluted with 500 g of water and neutralized at 70° C. with 128.7 g of 50% strength sodium hydroxide solution. The mixture was extracted three times with 1,2-dichloroethane, and the combined organic extracts were dried over sodium sulfate. Filtration and evaporation yielded a brown oil which was distilled under reduced pressure to give 101.8 g of colorless oil (82.1% of theory) of boiling point 104° C. (63 torr), which was identified by IR and NMR spectra as 1,3,4,5-tetramethylpyrazole.

We claim:

1. A process for preparing 3-methylpyrazole and its derivatives of the formula I

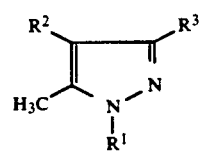

where $R^1$, $R^2$ and $R^3$ are each hydrogen or alkyl, cycloalkyl, aryl or aralkyl, which comprises reacting 2-butene-1,4-diol, 1-butene-3,4-diol or their acylates or ethynylalkylcarbinols of the formula II

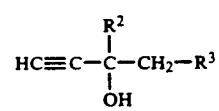

or their acylates in 30–100% by weight sulfuric acid with unsubstituted or substituted hydrazine of the formula III $$R^1-NH-NH_2 \quad \quad III$$

where $R^1$ has the abovementioned meaning, or its salts, in the presence of catalytic amounts of iodine or an iodine compound.

2. A process as claimed in claim 1, wherein the reaction is carried out at from 50° to 250° C.

3. A process as claimed in claim 1, wherein the reaction is carried out in the presence of from 0.01 to 10 mol % iodine based on the hydrazine III.

4. A process as claimed in claim 1, wherein the reaction is carried out at from 50° to 250° C. in the presence of from 0.01 to 10 mol % iodine based on the hydrazine III.

* * * * *